United States Patent
Ettema et al.

(10) Patent No.: US 7,655,798 B2
(45) Date of Patent: Feb. 2, 2010

(54) PROCESS OF MAKING CRYSTALLINE TYPE II ARIPIPRAZOLE

(75) Inventors: Gerrit J. B. Ettema, Nijmegen (NL); Raymond J. H. Westheim, Nijmegen (NL); Faysal Kalmoua, Oss (NL)

(73) Assignee: Synthon BV, Nijmegen (NL)

( * ) Notice: Subject to any disclaimer, the term of this patent is extended or adjusted under 35 U.S.C. 154(b) by 559 days.

(21) Appl. No.: 11/377,398

(22) Filed: Mar. 17, 2006

(65) Prior Publication Data

US 2006/0258673 A1    Nov. 16, 2006

Related U.S. Application Data

(60) Provisional application No. 60/662,552, filed on Mar. 17, 2005, provisional application No. 60/692,557, filed on Jun. 22, 2005, provisional application No. 60/739,640, filed on Nov. 26, 2005.

(51) Int. Cl.
*C07D 401/12* (2006.01)
*C07D 413/12* (2006.01)

(52) U.S. Cl. ..................... 544/363; 544/367

(58) Field of Classification Search ............. 544/363, 544/367
See application file for complete search history.

(56) References Cited

U.S. PATENT DOCUMENTS

| 4,734,416 | A | 3/1988 | Banno et al. |
| 5,006,528 | A | 4/1991 | Oshiro et al. |
| 2004/0058935 | A1 | 3/2004 | Bando et al. |
| 2006/0142299 | A1 | 6/2006 | Ettema et al. |
| 2006/0142579 | A1 | 6/2006 | Ettema et al. |

FOREIGN PATENT DOCUMENTS

| EP | 367141 | 1/1996 |
| WO | WO 03/026659 | 4/2003 |
| WO | WO 2005/058835 A2 | 6/2005 |

OTHER PUBLICATIONS

Fabrizia Grepioni, New Journal Of Chemistry; Polymorphism and crystal Forms; 2008, 32, 1657-1658.*
"Study on Crystal Transformation of Aripiprazole" The Fourth Japan-Korea Symposium on Separation Technology (1996), pp. 937-940.

* cited by examiner

*Primary Examiner*—James O Wilson
*Assistant Examiner*—Ebenezer Sackey
(74) *Attorney, Agent, or Firm*—Mark R. Buscher

(57) ABSTRACT

Crystalline aripiprazole Type II can be formed without solid state heat treatment. Instead a liquid is used such as in crystallizing from a solvent, especially 2-propanol, dimethyl sulfoxide, or a combination thereof with ethyl acetate, or in a solvent mediated solid-solid transformation, typically in ethyl acetate.

21 Claims, 2 Drawing Sheets

DSC scan (Type II)

XRPD spectrum (Type II)

PROCESS OF MAKING CRYSTALLINE TYPE II ARIPIPRAZOLE

This application claims the benefit of priority under 35 U.S.C. § 119(e) from each of (1) U.S. provisional application 60/662,552, filed Mar. 17, 2005, (2) U.S. provisional application 60/692,557, filed Jun. 22, 2005, and (3) U.S. provisional application 60/739,640, filed Nov. 26, 2005, each of which is incorporated herein by reference.

BACKGROUND OF THE INVENTION

The present invention relates to processes of making a crystalline form of 7-[4-[4-(2,3-dichlorophenyl)-1-piperazinyl]butoxy]-3,4-dihydrocarbostyril, also known as aripiprazole.

Aripiprazole is a compound of the formula (1).

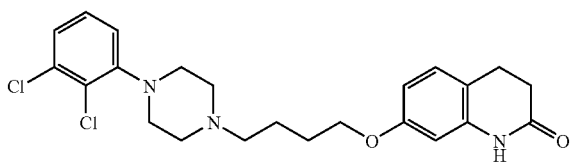

(1)

It is a commercially marketed, pharmaceutically active substance useful for treatment of schizophrenia. It is disclosed in EP 367141/U.S. Pat. No. 5,006,528. The commercially marketed product is the free base of the title compound (1).

Solid state aripiprazole was prepared in U.S. Pat. No. 5,006,528 by a two-fold recrystallization of crude aripiprazole from ethanol resulting in colorless flake crystals having a melting point of 139-139.5° C. In an article of Aoki (Study on Crystal Transformation of Aripiprazole, The Fourth Japan-Korea Symposium on Separation Technology, p.937 ff (1996)), this solid state form was designated as Type I aripiprazole and identified as an anhydrate. Aoki also teaches that the Type I aripiprazole may be converted into a Type II aripiprazole by heating at 130-140° C. for 15 hours. This product is an anhydrate as well with a melting point of 150° C. When both Type I and Type II aripiprazole were recrystallized from an alcoholic solvent containing water up to 20%, the product is an aripiprazole hydrate labeled as Type III by Aoki. Type III aripiprazole can be converted into Type I by heating at 80° C.

WO 03/26659 (EP 1330249) teaches that the Type I aripiprazole, the alleged original solid form of aripiprazole, is significantly hygroscopic. This document also disclosed other crystalline forms of aripiprazole. One form (Form A) is a hydrate, the remaining (Forms B-G) are low hygroscopic anhydrates, differing with arrangement of molecules in the crystalline lattice.

It would be desirable to form crystalline Type II of aripiprazole without the need for a heat treatment or heat conversion. In particular, it would be desirable to find an alternate, economically more advantageous process, which does not require long-term exposure to high temperatures.

SUMMARY OF THE INVENTION

The present invention is based on the discovery of how to form the solid state Type II aripiprazole without the use of a solid state heat treatment. Instead a liquid or solvent can be used such as by crystallizing Type II from a solvent or by a solvent-mediated solid-solid transition to form Type II in a solvent slurry.

Accordingly, a first aspect of the present invention relates to a process, which comprises crystallizing aripiprazole Type II from a solution of aripiprazole. More particular, the process comprises crystallizing aripiprazole dissolved in a solvent selected from the group consisting of 2-propanol, dimethyl sulfoxide, and mixtures thereof with ethyl acetate.

Another aspect of the invention relates to a process for making aripiprazole Type II, which comprises providing a solution which contains aripiprazole dissolved in a solvent selected from the group consisting of 2-propanol, dimethyl sulfoxide, and mixtures thereof with ethyl acetate; crystallizing the aripiprazole from the solution to form aripiprazole crystals; and recovering the crystals to obtain isolated crystalline aripiprazole Type II.

A third aspect of the invention relates to a solvent-mediated solid-solid conversion process of making aripiprazole Type II comprising stirring a suspension of aripiprazole Form B in a liquid medium, particularly in ethyl acetate, for a time sufficient to execute the solid-solid transformation from Form B to Type II.

A further aspect of the invention relates to a population of crystalline aripiprazole Type II particles, wherein at least 95% of said particles have a particle size of less than 200 microns, preferably between 50 and 200 microns in some embodiments and less than 50 microns in others. Such a population is conveniently made by one of the aforementioned processes, optionally with sieving.

DETAILED DESCRIPTION OF THE INVENTION

The invention is based on a surprising finding that aripiprazole Type II, contrary to the teachings in above-mentioned disclosures, can be formed by a process which does not require heating aripiprazole in solid state. Instead, aripiprazole Type II may be made in a liquid environment. This easier route of formation is especially desirable because it has now been discovered that Type II aripiprazole is not hygroscopic and thus would make an excellent pharmaceutical agent from the commercialization, production, and handling perspectives.

Figure 2:
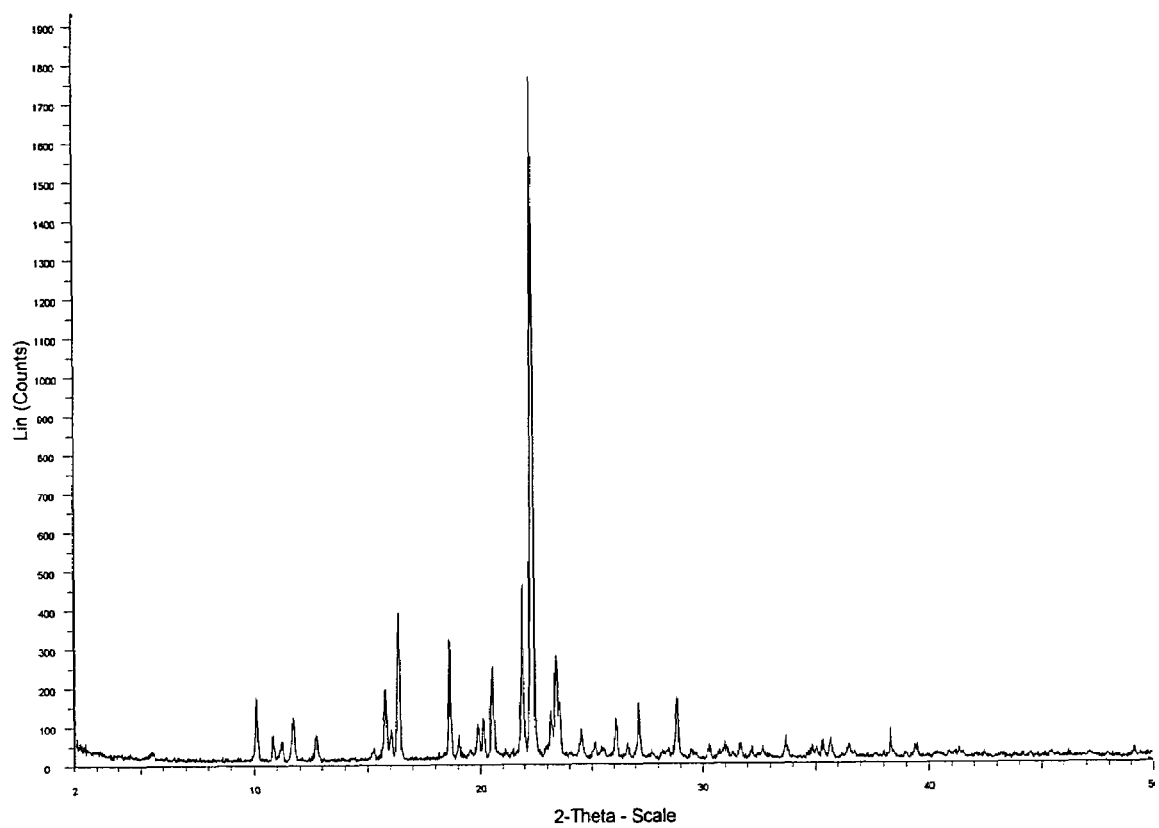
FIG. 2 represents an example of the XRPD pattern of aripiprazole Type II.

As used herein "Type II" of aripiprazole means a crystalline aripiprazole substance having an x-ray powder diffraction (XRPD) pattern that substantially corresponds to that of the Type II product as defined in the above cited article of Aoki. "Substantially corresponds" is meant to cover variations/differences in the pattern that would not be understood by a worker skilled in the art to represent a difference in crystal structure, but rather differences in technique, sample preparation, impurities, etc. An example of the XRPD of the Type II aripiprazole is shown on FIG. 2.

Figure 1:
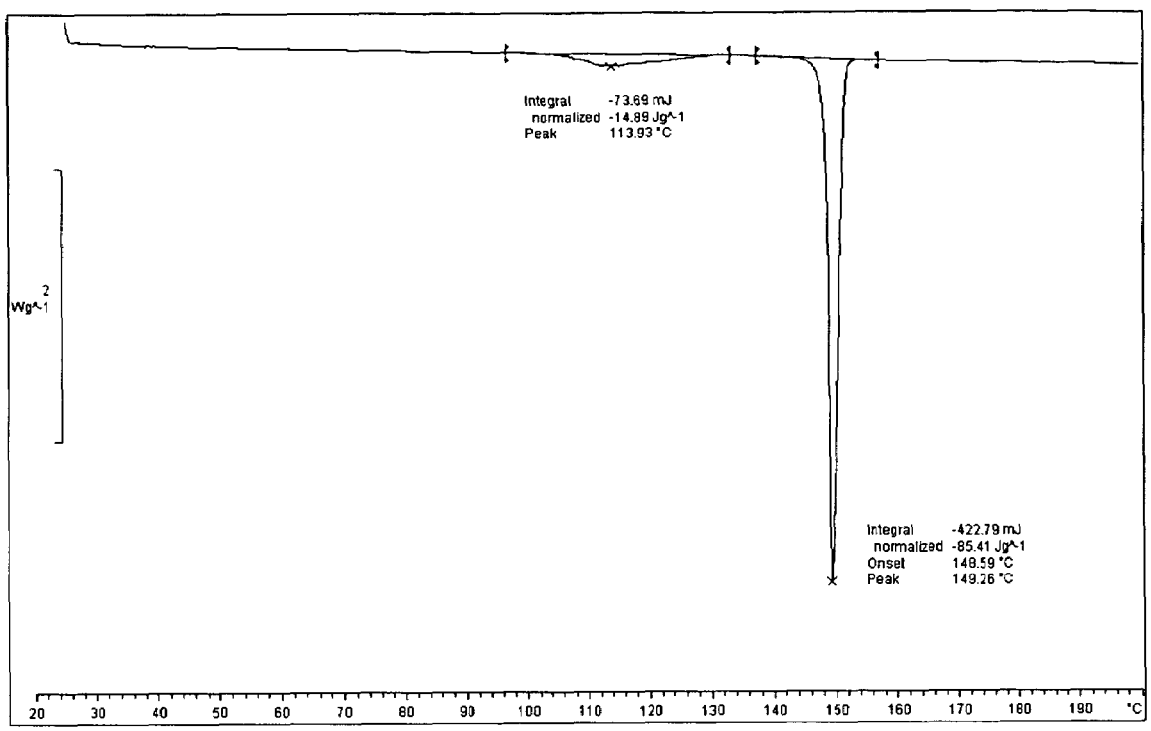
FIG. 1 represents an example of the DSC curve of aripiprazole Type II.

Typically the Type II aripiprazole will also have a single melting endotherm peak within the range of 145° C. to 150° C., especially around 148-149° C., measured using differential thermal analysis (DTA) or differential scanning calorimetry (DSC). An example of the DSC pattern of aripiprazole Type II is shown in FIG. 1. The DTA and DSC values should be used with a certain care as these types of data are dependant on measuring conditions such as heating rate, type of equipment, sample purity, sample loading, etc.

The Type II aripiprazole is a relatively stable crystalline form suitable for making pharmaceutical compositions on an industrial scale. The Type II aripiprazole (in pure state, i.e. free from other forms) is anhydrous, meaning it neither contains water or other solvent bound as part of the crystal lattice. This should be distinguished from wet crystals that have water or solvent adhered thereto. Such liquid is permitted (e.g., a "wet" or damp crystalline substance), so long as it is not part of the regular repeating unit of the crystal lattice. Generally, the Type II aripiprazole is non-hygroscopic. However, it can be hygroscopic if, inter alia, it is milled as discussed hereinafter.

The first process is crystallization of aripiprazole from a solvent. Such a process provides several advantages over heating aripiprazole in a solid state. The process is easily scaleable, well controllable and does not require thermal treatment at temperatures higher than 100° C. which minimizes the decomposition side products. Using a solvent also allows for purification of the product. This can be advantageous not only for crystallization of crude aripiprazole but also for relatively pure aripiprazole. Thus, Type II can be directly precipitated without the need to heat treat.

The solvents used in the present invention comprise 2-propanol, dimethyl sulfoxide, and combinations thereof. The list is not exhaustive. For example, additional solvents and/or antisolvents can also be present in the solution, as long as at least one of the aforementioned solvents is present. Generally the 2-propanol and/or dimethyl sulfoxide comprise at least 30% by volume, more typically at least about 50% by volume, of the solution. In one embodiment, ethyl acetate is additionally present, especially in combination with isopropanol, and typically within the range from 1 to 75% by volume, more typically 35 to 60% by volume of the total solvent system. Surprisingly, the additional presence of ethyl acetate to the 2-propanol solvent can provide a more robust crystallization media for precipitating Type II aripiprazole than 2-propanol alone. An aripiprazole solution containing approximately a 1:1 by volume mixture of isopropanol and ethyl acetate has been found to be a useful solvent system in terms of yield and purity. In all embodiments of the present invention, the solvent(s) is/are normally anhydrous, i.e. traces of water ordinarily present in a conventional batch should be controlled and, if necessary, removed. Typically the water content within the solvent system is less than 1%.

It is surprising that the use of the above mentioned solvents in crystallization allows the formation of Type II crystals of aripiprazole. In contrast, for example, it was discovered that alcohols such as methanol and ethanol produce alcoholates, that is solvates of aripiprazole (See U.S. Provisional Application 60/628,654, filed Nov. 18, 2004, the entire contents of which are incorporated herein by reference). While the bound solvent can be removed by heating, no Type II was obtained by such desolvation. Instead, Form B aripirazole was formed.

The crystallization of aripiprazole as Type II from the solution as described above can be carried out by techniques generally known in the art. That is, a solution containing crude aripiprazole dissolved in the solvent system of the invention is solidified by crystallizing the dissolved aripiprazole out of the solution. The aripiprazole-containing solution can be provided in a number of ways and is not particularly limited. For example, aripiprazole can be dissolved in the solvent or it can be synthesized in the solvent.

In this regard, any form of aripiprazole may be used as the starting material for crystallization; i.e., an isolated or unisolated crude product arisen from the synthesis of aripiprazole, which is called "crude aripiprazole" throughout this invention, or an aripiprazole product already isolated such as the Types I-III or Forms A-G as made by the techniques disclosed in the art, or an aripiprazole alcoholate such as a methanolate or a hemiethanolate as disclosed in Provisional Application 60/628,654. Typically the solvent is heated in order to increase the solubility of the crude aripiprazole. This includes forming a suspension of aripiprazole in the solvent and then heating until the solid dissolves or, alternatively, adding aripiprazole gradually into the already heated or hot solvent. A "hot" solvent has a temperature within the range of its boiling point to 20° C. less than its boiling point, typically from the boiling point to 10-15° C. below the boiling point of the solvent.

The concentration of aripiprazole in the solvent depends on the nature of solvent as well as the presence or absence of other dissolved or suspended components, e.g., reactants, side-products, etc. In general, the upper limit is the maximum concentration; i.e., the saturation concentration, at the boiling point of the solvent. Typically the concentration is at least about 20 to 250 mg/ml.

Once the solution containing aripiprazole has been provided, crystallization can, in general, be carried out by any convenient method. Usually the crystallization involves cooling the solution. The nucleation may be improved by adding a seeding crystal(s) or scratching the surface of the vessel. That is, the crystallization process may be induced or aided by adding small amounts of seed crystals of aripiprazole Type II.

The conditions of crystallization (concentration, cooling rate, etc.) may be controlled for the given solvent to result in the crystallization of aripiprazole Type II. With regard to isopropanol, it is possible to form Type I or Type II, depending on the conditions. In general, higher crystallization temperatures favor Type II of the present invention while lower temperatures favor Type I as described in U.S. Provisional Application 60/628,653, filed Nov. 18, 2004, the entire contents of which are incorporated herein by reference. Typically for isopropanol the crystals should initially be formed, e.g., become separated from the solution, at a temperature higher than 50° C. and more typically 65° C. or higher. If crystallization begins at a temperature less than 50° C., then Type I aripiprazole is generally more favored to be formed. In contrast to isopropanol, dimethyl sulfoxide solvent apparently does not readily formed Type I and thus can easily crystallize aripiprazole Type II in a more temperature independent fashion.

Other than as described above regarding the temperature concerns at the start of crystallization, the rate of cooling is not particularly limited and in general, it may affect the particle size of the formed crystals. A quicker rate of cooling generally leads to smaller crystals. A spontaneous cooling rate; i.e., allowing the solution to cool without special cooling or heating measures, as well as a linear cooling rate are generally preferred, although other cooling regimes are also contemplated for use in the present invention. The final temperature after cooling may also affect the particle size, the yield and/or the purity of the product.

As a result of crystallizing from the solvents of the invention, it is believed that aripiprazole Type II is easily and directly obtained. To confirm that the crystals are Type II, the crystals are isolated from the remaining solvent/solution and subjected to XRPD. The isolating of the crystals can be carried out by any conventional methods. In general, the solid crystalline material is recovered from the liquid portion such as by filtration or centrifugation, optionally washed such as with the solvent used or with the contrasolvent, and generally, though not necessarily, dried. The drying can be conducted in vacuo, with or with applying heat. It is an advantage of the process that the solvent may be removed without any long-term or high-temperature drying. The drying temperature advantageously does not exceed 60° C. and preferably does not exceed 40° C. Again, it is believed that the isolated wet crystals as well as the dried crystals are aripiprazole Type II.

Furthermore, it has been discovered that aripiprazole Type II may be prepared by a solvent-mediated solid-solid transformation of a suitable metastable solid state form of aripiprazole in a liquid medium. An example of the metastable solid state form of aripiprazole is the aripiprazole Form B (as defined in WO 03/26659). The transformation may occur by suspending the starting material in the liquid medium (which is a liquid in which the aripiprazole is not soluble or only sparingly soluble) and stirring the mixture for the time necessary for completing the conversion. The degree of conversion may be monitored by suitable methods. In general, heating or cooling the suspension is not necessary, but is not excluded. Typically the temperature is within the range of 0 to 30° C. such as ambient temperature. In an example, aripiprazole Form B may be converted into aripiprazole Type II by stirring in ethyl acetate suspension at room temperature for 15 hours. It is not suggested to use water or an alcohol within the medium, as hydrates or alcoholates of the aripiprazole might be formed, which is not suitable for the purpose of this invention.

After completing the conversion, the produced Type II aripiprazole may be isolated by any convenient way of separation from the medium, e.g. by filtration or centrifugation, and optionally dried to remove the rest of the liquids The processes of the present invention may be used for conversion of an undesired form of aripiprazole into the Type II aripiprazole, or for a purification of the insufficiently pure Type II aripiprazole. In particular, the crystallization process is well suited for this purpose as most of the impurities present in a crude starting material are well removed within the crystallization process of the present invention. The purification effect may be enhanced by using a surface active material prior to subjecting the aripiprazole solution to the crystallization, as such material may adsorb various impurities on its surface. Any conventional material, for instance activated carbon, Hyflo etc., may be used for this purpose. After treatment of the aripiprazole solution with such material, the material is normally removed such as by filtration, before carrying out crystallization. Thus, the process of the invention may be used to make essentially pure Type II of aripiprazole, i.e., essentially free from other forms of aripiprazole and/or from structurally related impurities. The essentially pure aripiprazole Type II comprises more than 98% of the Type II.

If the particle size distribution obtained as a result of the process of the invention is insufficient for the intended purpose, e.g., the dissolution profile, bioavailability of the aripiprazole, etc., is not within a desired range, then sieving of the crystal particles can be used to modify the population. In general, the useful population for pharmaceutical applications should contain at least 95% of particles having a particle size less than 200 microns, and in some embodiments less than 50 microns. For example, a population of aripiprazole Type II have a $d_{90}$ of 70 microns or less, more typically 50 microns or less, and frequently within the range of 18-50 microns, can be useful in making a tablet formulation. The desired population can be obtained by sieving with one or more sieves, if necessary. Milling should be avoided as polymorphic transitions may occur during milling. Unlike milling, the sieving process does not bring significant energy to bear on the aripiprazole crystalline material and the crystalline form is not usual adversely affected by the process.

This surprising fact relates not only to the aripiprazole Type II prepared by the process of the present invention, but also to the Type II prepared by methods of the prior art or any other process. Thus, a process of improving or adjusting particle size of aripiprazole Type II, characterized in that the aripiprazole Type II is subjected to sieving through a sieve of the desired mesh screen, is another aspect of the present invention. The desired fraction in some instances can be obtained by using two sieves with mesh sizes of a selected upper and lower limit, and fractions having particle sizes below and above the limits are discarded or reprocessed.

Aripiprazole Type II, sieved through a sieve of the mesh size of less than 200 microns, preferably through sieves of mesh sizes between 50 and 200 microns (=a population of particles of Aripiprazole Type II, wherein more than 95% of particles has a particle size less than 200 microns, typically between 50 and 200 microns) and also aripiprazole Type II, sieved through a sieve of the mesh size of less than 50 microns, can be advantageous from the standpoint of manufacturing and dissolution characteristics, particularly in making pharmaceutical tablets.

The aripiprazole Type II can be formulated into a pharmaceutical composition, especially a tablet or capsule, by combining the same with one or more pharmaceutically acceptable excipients. Generally the amount of aripiprazole is within the range of 1 to 50 mg per unit dose, and specifically 2, 5, 10, 15, 20, 25, or 30 mg per tablet. Suitable compositions are described in more detail in U.S. provisional application 60/739,640, which is incorporated herein by reference.

The present invention is more particularly described and explained by the following examples. It is to be understood, however, that the present invention is not limited to these examples and various changes and modifications may be made without departing from the scope of the present invention.

EXAMPLES

Reference Example: Method to Make Type II, Aoki et al 0.3 g of aripiprazole (Type I) was placed in a glass bottle of 10 ml with screw cap. The sample was annealed in an oven at 140° C. for 15 hours. The melt was slowly cooled to room temperature. Beige, opaque agglomerates of needle-like and fiber-like crystals were obtained. A small fraction of a brown glass was also present. The yield was not determined.
DSC: Irregular endothermic effects between 90-120° C. Melting peak around 147-150° C.
TGA: Only gradual mass loss above 220° C. (thermal degradation).
XRPD: Similar to the XRPD spectrum of Type II reported by Aoki et al.
HSM: Agglomerates of plate and fiber-like crystals, mainly opalescent to nearly opaque. Between 100-125° C. there is a clear solid-solid transition (crystal jumping and cracking). All crystals melt between 145-155° C.

Example 1

500 mg of aripiprazole (Type I) was suspended in 10 ml of ethyl acetate at room temperature. The suspension was stirred in a closed bottle with screw cap for about 24 hours. The crystals were isolated by filtration over a P3-glass filter (reduced pressure) and air-dried overnight at ambient conditions. A white, fine powder with some lumps was obtained. The yield was 410 mg.

DSC: faint (evaporation) endotherm between 50-90° C., an asymmetric endotherm between 115-135° C. and a melting peak around 148-149 C.

TGA: minimal mass loss below 80° C. (some water or residual solvent). Gradual mass loss above 220° C. (thermal degradation).

XRPD: Corresponds to Type II.

HSM: Small and irregular plates and fragments of plates.

Example 2

10 g of aripiprazole (Type I) was suspended in 50 ml of 2-propanol. The mixture was refluxed. To the hot suspension, 80 ml of 2-propanol was added. A clear solution was obtained. Reflux was continued for 10 minutes. The heating bath was removed, crystallization started after 4 minutes. (T=73° C.). The suspension was allowed to cool to room temperature and stirring was continued for 16 hours. The solid was isolated by filtration over a P3 glass filter and dried in a vacuum oven at 40 C for 2 hours. A white, crystalline powder with a yield of 9.42 g was obtained.

The crystals were dried at 90° C. and under vacuum for an additional 16 hours and analyzed.

DSC: An (asymmetric) endotherm between 95-135° C. and a melting peak around 148-149° C.

TGA: No mass loss up to 220° C. detected.

XRPD: Corresponds to Type II.

KF: no water detected

HSM: Mainly isolated plates. The particle size of the crystals is between 10-60 μm.

Example 3

1.01 g of aripiprazole (form B) was dissolved in 5 ml of DMSO at reflux. The hot solution was allowed to cool to room temperature. After 15 minutes, the flask was scratched with a spatula in order to induce nucleation sites. After an additional 30 minutes crystallization could be observed. Crystallization occurred in the next 45 minutes. Then, the crystals were isolated by filtration over a P3-glass filter (reduced pressure) and dried over the weekend at 40° C. and under vacuum. Shiny and colorless to slightly bluish or greyish crystals were obtained. The yield was 180 mg.

DSC: Irregular endotherm between 95-120° C. and a large melting peak around 148-150° C.

XRPD: Corresponds to Type II.

HSM: Thick needles and plates with different crystal dimensions.

Example 4

40.0 g of aripiprazole (Type I) was suspended in 520 ml of 2-propanol. The mixture was stirred and heated to reflux, resulting in a clear solution. Reflux was continued for about 45 minutes. The heating bath was removed and about 80-100 mg of aripiprazole, Type II, was added as seed in 4 steps. During addition of the seed, the solution was stirred. After the fourth addition, crystallization started. The inner temperature was about 68° C. The suspension was allowed to cool to room temperature (R.T.). After cooling, an additional 20-40 mg of aripiprazole, Type II, was added. The suspension was overnight stirred at R.T. The solid was isolated by filtration over a P3 glass filter and dried overnight in a vacuum oven at 40 C. An off-white, crystalline powder with a greyish or bluish tinge was obtained. The yield was 38.48 g.

DSC: Corresponds to Type II.

TGA: No mass loss up to 220° C. detected.

XRPD: Corresponds to Type II.

HSM: Prism-like plates and rods, typically between 20-200 μm. Few particles >200 μm.

Example 5

100 g Aripiprazole was suspended in 1.3 l of 2-propanol. The mixture was refluxed. After 1 hour a clear solution was obtained. The suspension was allowed to cool to room temperature, wherein at ±73° C. the solution was seeded with ±50 mg of aripiprazole Type II crystals. Crystallization started at that temperature. Stirring was continued for 16 hours. The solid was isolated by filtration over a P3 glass filter. The solid was dried in a vacuum oven at 40° C. for 24 hours. Yield: 94 g of Type II aripiprazole Example 6

140 g of aripiprazole was suspended in a mixture of 1 liter 2-propanol and 1 liter ethyl acetate. The stirred suspension was heated to reflux. A clear solution was obtained. Reflux was maintained for about 15 minutes. The stirred solution was allowed to cool to 55° C. At 55° C. the solution was seeded with 1 g of aripiprazole Type II crystals and precipitation commenced. The seeded solution was cooled to 4° C. in about 1 hour and 20 minutes. The resulting suspension was stirred at 0°- 4° C. for 30 minutes. The solid was isolated by filtration and dried in a vacuum oven at 40° C., <10 mbar for 16 hours. The yield was 125 g (89%) of Type II aripiprazole.

Each of the patents, patent applications, and journal articles mentioned above are incorporated herein by reference. The invention having been described it will be obvious that the same may be varied in many ways and all such modifications are contemplated as being within the scope of the invention as defined by the following claims.

We claim:

1. A process, which comprises:
    crystallizing aripiprazole Type II from a solution of aripiprazole dissolved in a solvent selected from 2-propanol, dimethyl sulfoxide, or mixtures thereof and optionally further comprising ethyl acetate.

2. The process according to claim 1, wherein the solvent has a water content of less than 1%.

3. The process according to claim 1, wherein said solvent is 2-propanol.

4. The process according to claim 1, wherein said solvent is a mixture of 2-propanol and ethyl acetate.

5. The process according to claim 4, wherein 2-propanol and ethyl acetate are present in an amount of about 1:1 by volume.

6. The process according to claim 1, which further comprises isolating said crystalline aripiprazole Type II from said solvent.

7. The process according to claim 6, wherein said isolating comprises filtering and/or drying.

8. A process for making aripiprazole Type II, which comprises:
    providing a solution which contains aripiprazole dissolved in a solvent selected from 2-propanol, dimethyl sulfoxide, or mixtures thereof and optionally further comprising ethyl acetate;
    crystallizing said aripiprazole from said solution to form aripiprazole crystals; and
    recovering the crystals from the solvent to obtain isolated crystalline aripiprazole Type II.

9. The process according to claim 8, wherein said providing step comprises forming said solution as part of a synthesizing route to make aripiprazole.

10. The process according to claim 8, wherein said providing step comprises dissolving aripiprazole in said solvent to form said solution.

11. The process according to claim 8, wherein said solvent is 2-propanol.

12. The process according to claim 8, wherein said solvent is a mixture of 2-propanol and ethyl acetate in an amount of about 1:1 by volume.

13. The process according to claim 8, wherein said crystallizing comprises cooling said solution.

14. The process according to claim 8, wherein said crystallizing comprises adding a seeding crystal of aripiprazole Type II.

15. The process according to claim 8, wherein said recovering step comprises separating said crystals from said solvent by filtration and drying said separated crystals.

16. The process according to claim 15, wherein said drying is carried out at a temperature of 40° C. or less.

17. The process according to claim 8, which further comprises sieving said crystalline aripiprazole Type II to obtain a desired particle size distribution.

18. A solvent-mediated solid-solid conversion process for making aripiprazole Type II, which comprises stirring a suspension of aripiprazole Form B in ethyl acetate for a sufficient time to obtain conversion to aripiprazole Type II.

19. The process according to claim 18, wherein said stirring is carried out at a temperature within the range of 0 to 30° C.

20. The process according to claim 19, which further comprises sieving said crystalline aripiprazole Type II to obtain a desired particle size distribution.

21. The process according to claim 13, wherein said solvent comprises at least about 50% by volume of 2-propanol; and wherein said crystallization begins at a temperature of 65° C. or higher.

* * * * *